(12) United States Patent
Nie et al.

(10) Patent No.: US 10,034,961 B1
(45) Date of Patent: Jul. 31, 2018

(54) COMPOSITE DURA SUBSTITUTE IMPLANT

(71) Applicant: Beijing Bonsci Technology Co., Ltd., Beijing (CN)

(72) Inventors: Hongtao Nie, Beijing (CN); Kai Zhang, Beijing (CN)

(73) Assignee: Beijing Bonsci Technology Co., Ltd., Beijing (CN)

( * ) Notice: Subject to any disclaimer, the term of this patent is extended or adjusted under 35 U.S.C. 154(b) by 0 days.

(21) Appl. No.: 15/405,066

(22) Filed: Jan. 12, 2017

(51) Int. Cl.
*A61L 27/18* (2006.01)
*A61L 27/56* (2006.01)
*A61L 27/24* (2006.01)
*A61L 27/32* (2006.01)
*A61L 27/54* (2006.01)
*A61L 27/12* (2006.01)

(52) U.S. Cl.
CPC ............... *A61L 27/18* (2013.01); *A61L 27/12* (2013.01); *A61L 27/24* (2013.01); *A61L 27/54* (2013.01); *A61L 27/56* (2013.01); *A61L 2430/00* (2013.01); *A61L 2430/02* (2013.01)

(58) Field of Classification Search
None
See application file for complete search history.

(56) References Cited

U.S. PATENT DOCUMENTS

| 2007/0254005 A1* | 11/2007 | Pathak | A61K 35/12 424/423 |
| 2008/0161927 A1* | 7/2008 | Savage | A61F 2/4455 623/17.16 |
| 2011/0274729 A1* | 11/2011 | Collins | A61L 27/34 424/400 |
| 2016/0081807 A1* | 3/2016 | Estes | A61F 2/30756 623/14.12 |

FOREIGN PATENT DOCUMENTS

WO      WO-2015092797 A1 *  6/2015  ............. A61L 31/06

* cited by examiner

*Primary Examiner* — Abigail Vanhorn
(74) *Attorney, Agent, or Firm* — RuyakCherian LLP

(57) ABSTRACT

A composite dura substitute implant for implantation at a dura defect site having a porous layer that provides an osteoconductive scaffold for bony ingrowth, a porous layer that provides a scaffold for regeneration of collagen at a dura surface, and an intervening layer for preventing cerebrospinal leakage is disclosed. The composite dura substitute implant facilitates regeneration of dura mater and promotes osteointegration with bony tissue. Methods of manufacturing such an implant and methods of treatment using such composite dura substitute implants are further disclosed.

21 Claims, 3 Drawing Sheets

COMPOSITE DURA SUBSTITUTE IMPLANT

Chinese Patent Application No. 201610884151.7 is incorporated by reference herein.

BACKGROUND OF THE INVENTION

Field of the Invention

This application is directed to composite dura substitute implant to repair and regenerate damaged dura tissue. More particularly, this application is directed to composite dura substitute implant formed of joined layers of porous bodies, methods of forming the same, and methods of treatment.

Description of the State of the Art

The human brain and spinal cord are covered with meningeal membranes whose integrity is critical to the operation of the central nervous system. FIG. 1 depicts an illustration of the human brain. In particular, the meningeal membrane comprises three overlapping layers of tissue, which are in order from outside to inside, the dura mater (or dura), the arachnoid, and the pia mater. Dura mater refers to the membranes found between the skull and the brain and between the vertebral column and the spinal cord. When the integrity of a person's meningeal membranes is intentionally or accidentally compromised, serious consequences may ensue, unless the membranes can be repaired.

Defects of the dura mater or dura defect is a common clinical issue resulting from trauma, inflammation, tumor resection and congenital malformations. Complications such as cerebrospinal fluid leakage, infections, meningitis, and epilepsy can be generated due to inadequate closures of the dura after neurosurgery. Defects of the dura mater can produce a variety of undesirable consequences such as brain herniation, adhesion formation between the neural tissue and the overlying structures, pseudomeningocele, cortical scarring, cerebrospinal fluid fistulas and wound infection with potential propagation to the brain parenchyma. As a result, there has been a continuing need to develop novel clinical strategies for dura closure. During the past years, a variety of dura substitute implants have been developed and used for dura repair.

Duraplasty is a plastic or reconstructive operation on the dura mater. Repair of a dura defect may require application of a dura substitute (commonly referred to as a dural patch), especially, for example, when a large defect is created in the dural envelope in the course of a surgical procedure (e.g., tumor removal) or as a result of trauma. Also, congenital anomalies such as Arnold Chiari malformation and myelomeningoceles and spinal dysraphic states may require a duraplasty as part of the repair.

Repairing damaged meningeal membranes has largely focused on implantable and/or resorbable dura substitutes which are grafted over the damaged dura mater and are designed to replace and/or regenerate the damaged tissue. Dura substitute implants are used clinically to both regenerate damaged dura mater after neurosurgery to prevent cerebrospinal fluid (CSF) leakage and adhesion.

Dura substitute implants are typically made from the following sources: (1) human autograft or allograft, (2) synthetic fabric materials such as non-degradable ePTFE (Gore-Tex) or biodegradable polymers such as PLA/PGA (Vicryl), and (3) biological materials such as collagens which are generated from animal sources such as bovine/porcine tissues.

There are a number of issues with current dura substitute implants. Both autografts and allografts have limited supply. Fascia lata and galea periosteal tissue are commonly used autografts in the surgical repair of dural defects. The use of allografts such as lyophilized cadaveric dural graft has been associated with Creutzfeldt-Jakob disease (CJD). The risk of transmission of the CJD agent has led to the ban of cadaveric dura mater products. Non-degradable synthetic materials are bioinert and do not integrate well with tissues. Degradable synthetic materials typically generate acidic by-products which may induce inflammation reactions. In addition, degradable synthetic materials may either degrade or lose mechanical strength too fast or too slowly. Both non-degradable and degradable synthetic materials have been rejected clinically because of local tissue reactions, excessive scar formation, meningitic symptoms, or hemorrhage risk. Biological materials based on porcine intestinal submucosa and bovine pericardium have also been used as dura substitutes. However, such xenogenic materials are nonresorbable, and may result in a risk of complications associated with infection and immunorejection. Degradable collagen matrices based on bovine tendons have raised concerns of rate of degradation, low mechanical strength and usage with sutures.

SUMMARY

Embodiment one of the present invention include an implantable dura substitute implant comprising of: a first porous layer comprising a synthetic non-collagen polymer and an osteoconductive material; a second porous layer comprising the synthetic non-collagen polymer and a collagen component; and a middle layer between the first porous layer and the second porous layer, wherein the middle layer is nonporous or has a lower porosity than the first porous layer and the second porous layer, wherein the first porous layer is for contacting bone tissue and the second porous layer is for contacting dura mater upon implantation of the implant at the site of a dural defect in a patient, wherein upon implantation of the osteoconductive material facilitates growth of bone in the first porous layer from the bone tissue and the collagen facilitates dura repair and regeneration in the second porous layer, and wherein the middle layer reduces or prevents leakage of cerebrospinal fluid (CSF) from the second porous layer and dura mater.

Embodiment one includes any one or any combination of the following: wherein the synthetic non-collagen polymer is selected from the group consisting of poly aryl ether ketone (PAEK), polyethylene (PE), polyethylene terephthalates (PET), polymethylmethacrylate (PMMA), expandable polytetrafluoroethylene (ePTFE), poly(lactic acid) (PLA), poly(glycolic acid) (PGA), and poly(lactic acid)-co-poly (glycolic acid) (PLGA); wherein the PAEK is selected from the group consisting of poly ether ether ketone (PEEK) and poly ether ketone ketone (PEKK); wherein the PE is ultra-high molecular weight polyethylene (UHMWPE); wherein the collagen component is derived from bovine tissue or porcine tissue or human tissue; wherein the first porous layer is composed of fibers comprising the non-collagen polymer, wherein the fibers comprise a coating including the osteoconductive material; wherein the second porous layer is composed of fibers comprising the non-collagen polymer; wherein the fibers comprise a coating including the collagen; wherein the non-collagen polymer is PEKK; wherein the non-collagen polymer is UHMWPE; wherein the first porous layer and the second porous layer have a porosity between 20 and 90%; wherein the porosity is between 30 and 80%; wherein the porosity is between 40 and 70%; wherein a pore size of the first porous layer and the second porous layer is between 10 and 1000 microns; wherein the pore size is between 50 to 800 microns; wherein the pore size is between 50 to 500 microns; wherein middle layer is nonporous; wherein the middle layer has a porosity between 0 and 10%; wherein the osteoconductive material comprises a bone-like apatite material or a calcium phosphate material; wherein the non-collagen polymer of the middle layer interpenetrates pores of the first porous layer at an interface between the middle layer and the first porous layer; and wherein the non-collagen polymer of the middle layer interpenetrates pores of the second porous layer at an interface between the middle layer and the second porous layer.

Embodiment two of the present invention includes a method of making a dura substitute implant comprising the steps of: bonding a first porous polymeric layer to a third polymeric layer at a surface of the third polymeric layer; bonding a second porous polymeric layer to the third polymeric layer at an opposing surface of the third polymeric layer, wherein the third polymeric layer is nonporous or has a porosity sufficiently low that upon implantation of the implant the third polymeric layer prevents leakage of cerebrospinal fluid; and impregnating the first porous polymeric layer with a osteoconductive material; and impregnating the second porous polymeric layer with collagen.

Embodiment two includes any one or any combination of the following: wherein bonding the first porous polymeric layer to the third polymeric layer comprises heating the first porous polymeric layer or the third polymeric layer and applying a compressive force between the third polymeric layer and the first porous polymeric layer which causes polymeric material of the third polymeric layer to penetrate into pores of the first porous polymeric layer; wherein bonding the second porous polymeric layer to the third polymeric layer comprises heating the second porous polymeric layer or the third polymeric layer and applying a compressive force between the third polymeric layer and the second porous polymeric layer which causes polymeric material of the third polymeric layer to penetrate into pores of the second porous polymeric layer; wherein the second porous polymeric layer is impregnated through exposure of the second porous polymeric layer to a collagen solution or dispersion; wherein the exposure to the collagen solution or dispersion is by dip coating the second porous polymeric layer in the collagen solution followed by drying in a vacuum oven; wherein collagen content of the collagen solution is 0.01 to 5 wt %; wherein the first porous polymeric layer is impregnated through exposure of the first porous polymeric layer to a solution comprising calcium and phosphate ionic groups; wherein the exposure of the first porous polymeric layer is by soaking the first porous polymeric layer in a saline solution comprising calcium and phosphate salts or by sequentially soaking the first porous polymeric layer in a saline solution comprising calcium and a solution of phosphate; wherein the calcium salts are selected from the group consisting of calcium chloride, calcium fluoride, calcium nitride, and any combination thereof; wherein a concentration of the calcium salts are 0.001 to 1 mol/L; wherein a concentration of the phosphate salts is 0.001 to 1 mol/L.

Embodiment three of the present invention includes a method of treating a dural defect in a patient having damaged dura mater comprising: implanting a dura substitute implant on a site of the dural defect of the brain of the patient, wherein the dural defect is in contact with a bottom porous layer of the implant comprising a synthetic non-collagen polymer and collagen and the collagen facilitates dura repair and regeneration tissue within the bottom porous layer, wherein bone tissue is in contact with a top porous layer of the implant comprising the synthetic non-collagen polymer and an osteoconductive calcium phosphate material which causes bone growth in the top porous layer and integrates the top porous layer with cranial tissue, and wherein leakage of cerebrospinal fluid from the site is prevented by an intervening layer between the top and bottom porous layers comprising the synthetic non-collagen polymer, one may want the bony ingrowth or an osteoconductive structure to be a thickness of 1 mm or thicker.

Embodiment three includes any one or any combination of the following: wherein the implant conforms to the dura tissue at the implant site; wherein the collagen promotes fibroblast activity and acts as a scaffold for cells to deposit new collagen; wherein implanting comprises securing the implant over the site with sutures; and wherein implanting comprises securing the implant over the site without sutures.

DETAILED DESCRIPTION

Figure 1:
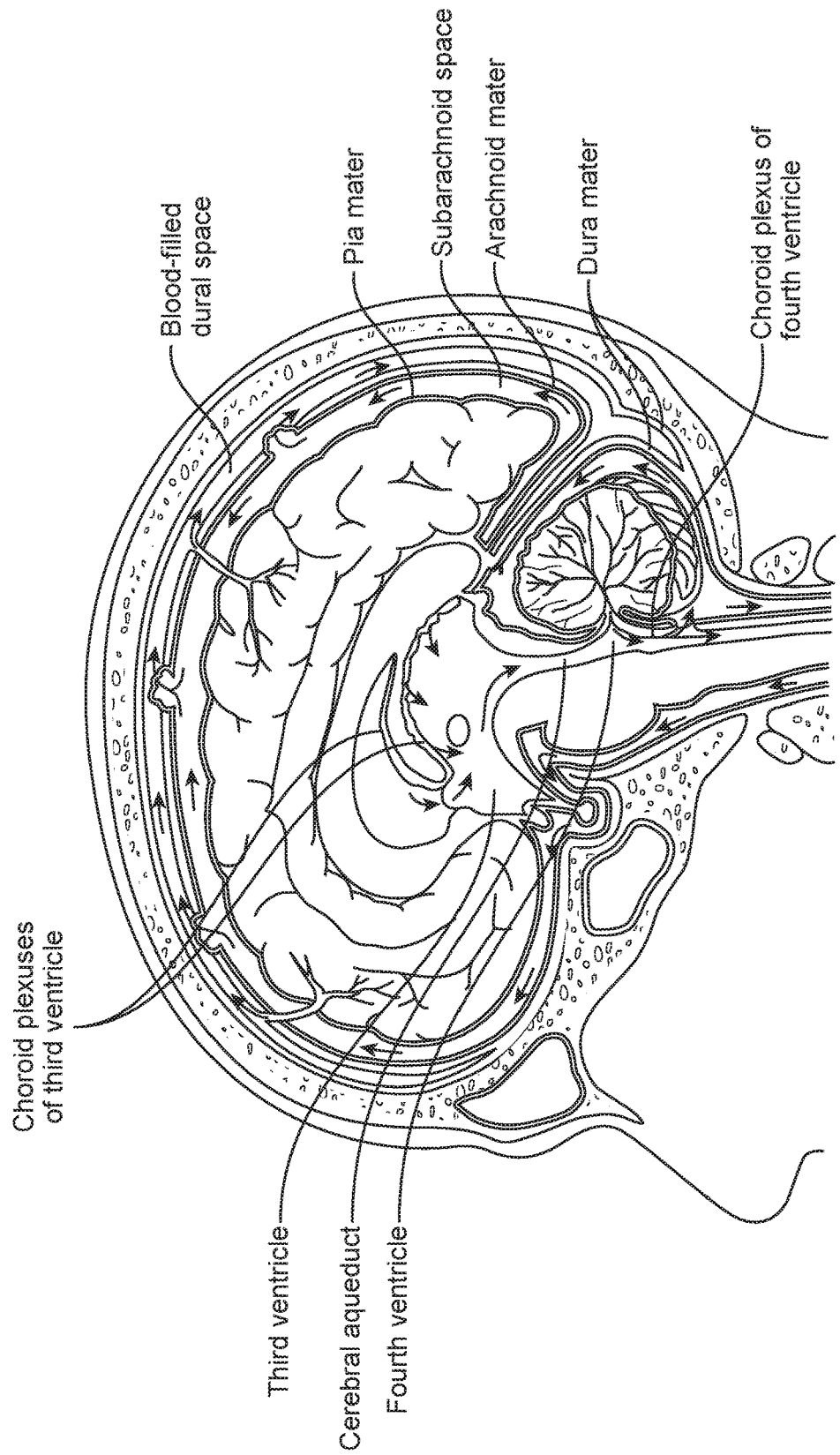
FIG. 1 depicts an illustration of the human brain.

A duraplasty is a plastic or reconstructive operation on the dura mater to repair a dural defect involving application of a dura substitute to the dura mater. The dura substitute can take the form of a thin membrane that is sized to fit over the dural defect. The dura substitute is placed over the dural defect which is exposed through an opening in the cranium. The purpose of the dura substitute is to replace damaged tissue, regenerate the damaged tissue, or both.

Repairing damaged meningeal membranes has largely focused on implantable and/or resorbable dura substitutes which are grafted over the damaged dura mater. Dura substitute implants are used clinically to both prevent cerebrospinal fluid (CSF) leakage, adhesion, and regenerate damaged dura mater after neurosurgery.

There are several important characteristics of dura substitutes. First, the dura substitute must prevent leakage of cerebrospinal fluid (CSF) from the brain. CSF is a clear, colorless body fluid found in the brain and spine. The CSF occupies the subarachnoid space (between the arachnoid mater and the pia mater) and the ventricular system around and inside the brain and spinal cord. Second the dura substitute should be durable, strong, and pliable. Durability refers to the ability to withstand wear, pressure, and handling both before and after implantation. Pliability or flexibility is important so that the implant can conform to tissue surfaces at the implant-dural interface and the implant-cranium interface. Third, the dura substitute should also be able integrate with tissues on both the dura side and the cranial side. On the dura side, the integration includes promoting regeneration of tissue through growth of collagen in and on the implant, while on the cranial side, the implant should provide for bone ingrowth within the implant. Fourth, the implant it may be preferable to degrade gradually along with tissue regeneration. Fifth, the dura substitute should have high biocompatibility such as low risk of infection, no immunological response, and no foreign body response. Six, the dura substitute should have versatility in surgical handling. In particular it should accommodate both suture and non-suture onlay techniques.

The present invention includes composite dura substitute implants for implantation at a dura defect site which provides some or all of the above advantages. In particular various embodiments of the present invention include a dura substitute that upon implantation has a porous layer adjacent to the cranium that provides an osteoconductive scaffold for bony ingrowth, a porous layer adjacent to the dura surface that provides a scaffold for regeneration of collagen, and an intervening layer for preventing CSF leakage. Osteoconduction refers to bone growth on a surface, for example, within the pores of a material. Therefore, the composite dura substitute implant both facilitate regeneration of dura mater and promote osteointegration with bony tissue. The embodiments further include methods of manufacturing of such implants and methods of treatment using such composite dura substitute implants.

Embodiments of the present invention include an implantable dura substitute implant having a first or top porous layer including a synthetic non-collagen polymer (SNCP) and a mineral component, a second or bottom porous layer including a synthetic non-collagen polymer and a collagen component, and a middle layer between the first porous layer and the second porous layer. The dura implant may have the form of a film, membrane, or sheet such that the layers make up all or part of the thickness of the film, membrane, or sheet.

The middle layer may be nonporous or have lower porosity than the first porous layer and the second porous layer. Upon implantation at the site of a dura defect in a patient, the first or top porous layer may be in contact with or on the side of bone tissue and the second or bottom porous layer may be in contact or on the side of dura mater upon implantation of the implant.

Figure 2:
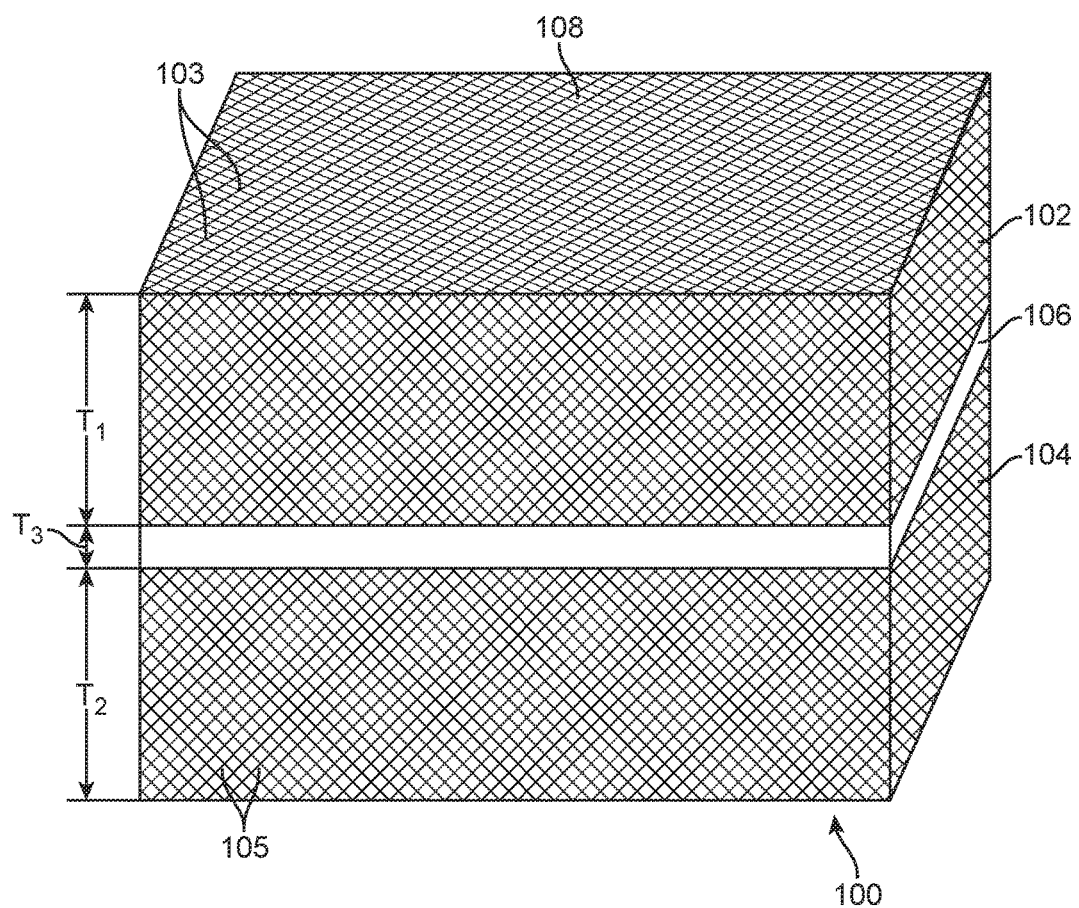
FIG. 2 is a perspective schematic representation of a section of an exemplary composite implant for placement between the skull and dura mater.

FIG. 2 is a perspective schematic representation of a section 100 of an exemplary composite implant for placement between the skull and dura mater. Section 100 includes a top porous layer 102, a bottom porous layer 104 and a middle layer 106. A top surface 108 of top porous layer 102 contacts the skull and a bottom surface (not shown) of bottom layer 104 contacts the dura mater upon implantation. Top porous layer 102 is a fabric layer made up of a plurality of fibers 103 composed of a SNCP and bottom layer 104 is a fabric layer made up of a plurality of fibers 105 composed of the SNCP. Fibers 103 are coated with an osteoconductive material and fibers 105 are coated with collagen. Middle layer 106 is a nonporous layer of the SNCP.

Top porous layer 102 has a thickness $T_1$, bottom layer 104 has a thickness $T_2$, and middle layer 106 has a thickness $T_3$. $T_1$ may be between 0.05 and 3 mm, or more narrowly, 0.05 to 1 mm, 1 to 1.5 mm, 1.5 to 2 mm, 2 to 2.5 mm, or 2.5 to 3 mm. $T_2$ may be between 0.05 and 3 mm, or more narrowly, 0.05 to 0.5 mm, or 0.5 to 1 mm, 1 to 2 mm, or 2 to 3 mm. $T_3$ may be between 0.001 and 1 mm, or more narrowly, 0.001 to 0.01 mm, 0.01 mm to 0.1 mm, 0.1 to 0.5 mm, or 0.5 to 1 mm.

The SNCP may make up a majority by weight, volume, or both of each of the first porous layer and the second porous layer. The SNCP may be considered a matrix and the collagen or mineral component may be dispersed or distributed within the SNCP of the respective layers. The weight percent of the collagen in the bottom layer may be 0.1 to 50%, or more narrowly, 0.1 to 1%, 1 to 5%, 5 to 10%, 10 to 20%, 20 to 30%, 30 to 40%, or 40 to 50%. The weight percent of the mineral component in the top layer may be 0.1 to 67%, or more narrowly, 0.1 to 5%, 5 to 10%, 10 to 20%, 20 to 30%, 30 to 40%, 40 to 50%, 50 to 60%, or 60 to 67%.

The mineral component promotes or facilitates growth of bone in the first porous layer from the bone tissue and the collagen promotes or facilitates dura repair and regeneration in the second porous layer. The middle layer reduces or prevents leakage of CSF from the second porous layer and dura mater. The middle layer may have some porosity, but sufficiently low that leakage of CSF is prevented.

Synthetic polymers refers to human-made polymers and may include thermoplastics, thermosets, and elastomers. A thermoplastic refers to a polymer that becomes pliable or moldable above a specific temperature, such as a glass transition temperature (Tg) and solidifies upon cooling. A thermosetting polymer refers to a prepolymer material which cures irreversibly upon exposure to radiation or elevated temperature. An elastomer is a polymer with viscoelasticity, i.e., having both viscosity and elasticity, and very weak inter-molecular forces, generally having low Young's modulus and high failure strain compared with other materials.

Each of the top porous layer, bottom, and middle layer may be made of the same synthetic non-collagen polymer (SNCP). Alternatively, the top and bottom layers may be made of the same SNCP, while the middle layer may be made of a different SNCP.

In some embodiments, the SNCP is a polyaryletherketone (PAEK) which refers to plastics that are characterized by phenylene rings that are linked via oxygen bridges (ether and carbonyl groups (ketone)). PAEK polymers include polyether ether ketone (PEEK), polyetherketoneketone (PEKK), poly(ether ether ketone ketone) (PEEKK), and PEKEKK (polyetherketoneetherketoneketone).

In particular, PEEK is a semicrystalline thermoplastic with mechanical and chemical resistance properties that are retained to high temperatures. PEEK has a Young's modulus is 3 to 4 GPa, tensile strength 90 to 100 MPa. Glass transition temperatures (Tg's) and melting temperatures (Tm's) are given in Table 1. PEKK's glass transition temperature (Tg) is 162° C.

In some embodiments, the SNCP is a non-fluoropolymer.

In other embodiments, the SNCP is polyethylene (PE), ultrahighmolecular weight polyethylene (UHMWPE) (e.g., Dyneema®), a polyethylene terephthalates (PET), polymethylmethacrylate (PMMA), and expandable polytetrafluorethylene (ePTFE).

TABLE 1

Glass Transition and Melting Temperatures of Some Suitable Polymeric Materials

| Material | UHMWPE | PMMA | PEEK | PET |
|---|---|---|---|---|
| Tg (° C.) | ~−160 | ~105 | ~143 | ~65 |
| Tm (° C.) | ~135 | — | ~340 | ~260 |

The SNCP may be a biostable polymer like PAEK or PE. In further embodiments, the SNCP is a biodegradable polymer including, but not limited to poly(lactic acid) (PLA), poly(L-lactide acid), poly(DL-lactide acid), poly(glycolic acid) (PGA), and poly(lactic acid)-co-poly(glycolic acid) (PLGA). A biodegradable polymer is a polymer that undergoes hydrolysis, enzymatic degradation, or both upon exposure to bodily fluids. For purposes of this disclosure, biodegradable is synonymous with bioabsorbable, bioresorbable, or bioerodible. A biostable polymer is a polymer that is not biodegradable.

The mineral component may be a bioactive calcium phosphate compound, such as a bone-like apatite material. The calcium phosphate material includes, but is not limited to, monocalcium phosphate $(Ca(H_2PO_4)_2$, dibasic calcium phosphate (hydrous or anhydrous $(CaHPO_4.2H_2O$ or $CaHPO_4)$, tricalcium phosphate (tribasic calcium phosphate or tricalcium phosphate) $(Ca_3(PO_4)_2)$, hydroxyapatite $(Ca_5(PO_4)_3(OH))$, apatite $(Ca_{10}(PO_4)_6(OH, F, Cl, Br)_2O)$, octacalcium phosphate $(Ca_8H_2(PO_4)_6.5H_2O)$, biphasic calcium phosphate (biphasic mixture of tricalcium phosphate and hydroxyapatite), tetracalcium phosphate $(Ca_4(PO_4)_2O)$, amorphous calcium phosphate, or any combination thereof.

The collagen may be derived from the structural protein in the extracellular space in the various connective tissues in animal bodies. For example, the collagen is derived from bovine tissue or porcine tissue.

The collagen protein is composed of a triple helix, which generally consists of two identical chains ($\alpha$1) and an additional chain that differs slightly in its chemical composition ($\alpha$2). The amino acid composition of collagen is atypical for proteins, particularly with respect to its high hydroxyproline content. The most common motifs in the amino acid sequence of collagen are glycine-proline-X and glycine-X-hydroxyproline, where X is any amino acid other than glycine, proline or hydroxyproline.

In some embodiments, the first porous layer, second porous layer, or both includes a fabric layer composed of fibers or yarn made of the SNCP. The fabric layer may be formed by weaving, knitting, electrospinning, or braiding yarns or fibers. Electrospinning is a fiber production method which uses electric force to draw charged threads of polymer solutions or polymer melts up to fiber diameters in the order of some ten nanometers. Electrospinning shares characteristics of both electrospraying and conventional solution dry spinning of fibers.

Fabric layers for medical applications may be obtained from Atex Technologies Inc., Pinebluff, N.C. The porous structure of a fabric layer arises from void spaces between the fibers of the fabric. The pore structure of the fabric may be an open cell structure.

Weaving refers to interlacing two yarns so that they cross each other at right angles to produce a woven fabric. A woven fabric includes warp yarns in the longitudinal direction and weft yarns in the crosswise direction. The warp and weft yarns may be the same fiber and same size or they may be different in fiber type and size.

Knitting refers to constructing fabric by interlocking a series of loops of one or more yarns. A braid is a complex structure or pattern formed by intertwining three or more strands of flexible material such a fiber or yarn. A braid is usually long and narrow, with each component strand functionally equivalent in zigzagging forward through the overlapping mass of the others.

The fabric layer may also be a nonwoven fabric broadly defined as a sheet or web structure bonded together by entangling fibers or filaments (and by perforating films) mechanically, thermally or chemically. Nonwoven fabric layers may be flat, porous sheets that are made directly from separate fibers or from molten plastic or plastic film. The fibers in a non-woven may be oriented in one direction or randomly throughout the fabric.

Multiple fabric layers can be combined to achieve desired strength, elongation and other mechanical properties. Porosity can be controlled by varying fiber diameter, fiber density, fiber orientation and additional mechanical processing.

In some embodiments, the first or top porous layer includes the mineral component, but no collagen component. Alternatively, the top layer includes both the mineral component and the collagen component.

The mineral component may be impregnated into the top fabric layer. In particular, the fibers may have a coating of the mineral component. The mineral component may be uniformly impregnated throughout a thickness of the top porous layer.

The collagen component may be impregnated into the bottom fabric layer or both the bottom and top fabric layers. In a similar manner, the fibers may have a coating of the collagen component. The mineral component may be uniformly impregnated throughout a thickness of the bottom fabric layer. When the top fabric layer includes both the mineral and collagen components, the mineral component may be coated over the collagen component, the collagen component may be coated over the mineral component, or the coating may be a homogeneous or inhomogeneous mixture of the collagen and mineral component.

In alternative embodiments, the top porous layer, bottom porous layer, or both may be a porous polymer foam that includes voids or pockets, channels, or both. A polymer foam may be formed by trapping pockets of gas in a polymer liquid or solid. For example, a porous PEEK may be fabricated using compounding with porogen filler, extrusion, and subsequent extraction with water at supercritical temperatures and pressures. The porous network may be an open-cell structure in which the void spaces are interconnected.

The mineral component or collagen component may impregnated into a polymer foam layer. In some embodiments, the component may coat the inside surface of the pores which partially fills the pore structure of the foam. In some embodiments, a top polymer foam layer may include both the collagen and mineral components. The collagen may be coated over the mineral component, the mineral component may be over the collagen component, or the mineral and collagen components may be a homogeneous or inhomogeneous mixture.

Alternatively, the mineral component, collagen, or both may be blended or mixed throughout the SNCP of the polymer foam. The mineral component or collagen may be blended with the SNCP, even prior to or while the porous network of the polymer foam is formed. For example, a blend of the SNCP and collagen or SNCP and the mineral component may be formed by melt processing or by precipitation from a solution. The pores of foam can be formed during the processing or after.

The middle layer of the composite implant may be a sheet or film that is nonporous or very low porosity. The sheet or film may be formed by a melt processing method such as by extrusion or injection molding. Alternatively, the middle layer may be fabric layer of very low porosity, for example, fabric layer of tightly woven or knitted fibers. The sheet or film may be nonwoven, such as nonwoven fibers.

The first porous layer and the second porous layer have a porous network of a plurality of pores. The layers may be porous throughout the layers. The porosity of the first porous layer or second porous layer may be between 20 and 90%, or more narrowly, between 30 and 80%, or between 40 and 70%. The average pore size of the first porous layer or the second porous layer may be between 10 and 1000 microns, or more narrowly between 50 to 800 microns, or between 50 to 500 microns. The middle layer may be nonporous or have a porosity that is not measureable. The middle layer may have a porosity less than 1%, 0.01 to 0.1%, 0.01% to 1%, or 1 to 10%.

Embodiments of a method of treating a dural defect in a patient having damaged dura mater may include implanting a dura substitute implant on a site of the dural defect of the brain of the patient. Prior to implantation, the dural defect is exposed with a portion of the cranium around the defect absent or removed. The implant is disposed over the dural defect and conforms to the dura tissue at the implant site. A bottom porous layer including an SNCP and collagen may be in contact with the dura tissue. The implant may be secured with or without suturing The secured implant may then be covered with cranial tissue. Bone tissue of the cranium is may be in contact with a top porous layer of the implant including the synthetic non-collagen polymer and an osteoconductive calcium phosphate material.

The collagen facilitates dura repair and regeneration tissue within the bottom porous layer. Collagen provides repair and regeneration by promoting fibroblast activity and acts as a scaffold for cells to deposit new collagen in the pores. The osteoconductive calcium phosphate material causes bone growth in the top porous layer and integrates the top porous layer with cranial tissue. Leakage of CSF from the site is prevented by an intervening layer between top and bottom porous layers which includes the synthetic non-collagen polymer.

Embodiments of the composite dura substitute implant may be made by first fabricating composite structure including the top porous layer, middle layer, and bottom porous layer prior to impregnating the layers with the mineral and collagen components as described.

Various embodiments of a method of making a dura substitute implant include bonding a first porous polymeric layer to a third polymeric layer at a surface of the third polymeric layer and bonding a second porous polymeric layer to the third polymeric layer at an opposing surface of the third polymeric layer. The first porous polymeric layer may be a top layer and the second porous polymeric layer maybe a bottom layer of the implant.

The third polymeric layer may be nonporous or has a porosity sufficiently low that upon implantation the third polymeric layer prevents leakage of CSF. The method further includes impregnating the first porous polymeric layer with an osteoconductive calcium phosphate material and impregnating the second porous polymeric layer with collagen.

In some embodiments, heating bonding with pressure may be used for the bonding steps. Bonding the first porous polymeric layer to the third polymeric layer may include heating the first porous polymeric layer or the third polymeric layer and applying a compressive force between the third polymeric layer and the first porous polymeric layer which may cause polymeric material of the third polymeric layer to penetrate into pores of the first porous polymeric layer. In a similar manner, bonding the second porous polymeric layer to the third polymeric layer includes heating the second porous polymeric layer or the third polymeric layer and applying a compressive force between the third polymeric layer and the second porous polymeric layer which causes polymeric material of the third polymeric layer to penetrate into pores of the second porous polymeric layer. The penetration of the polymeric material results in an interface layer between the third polymeric layer and the first and second porous polymeric layers.

Figure 3:
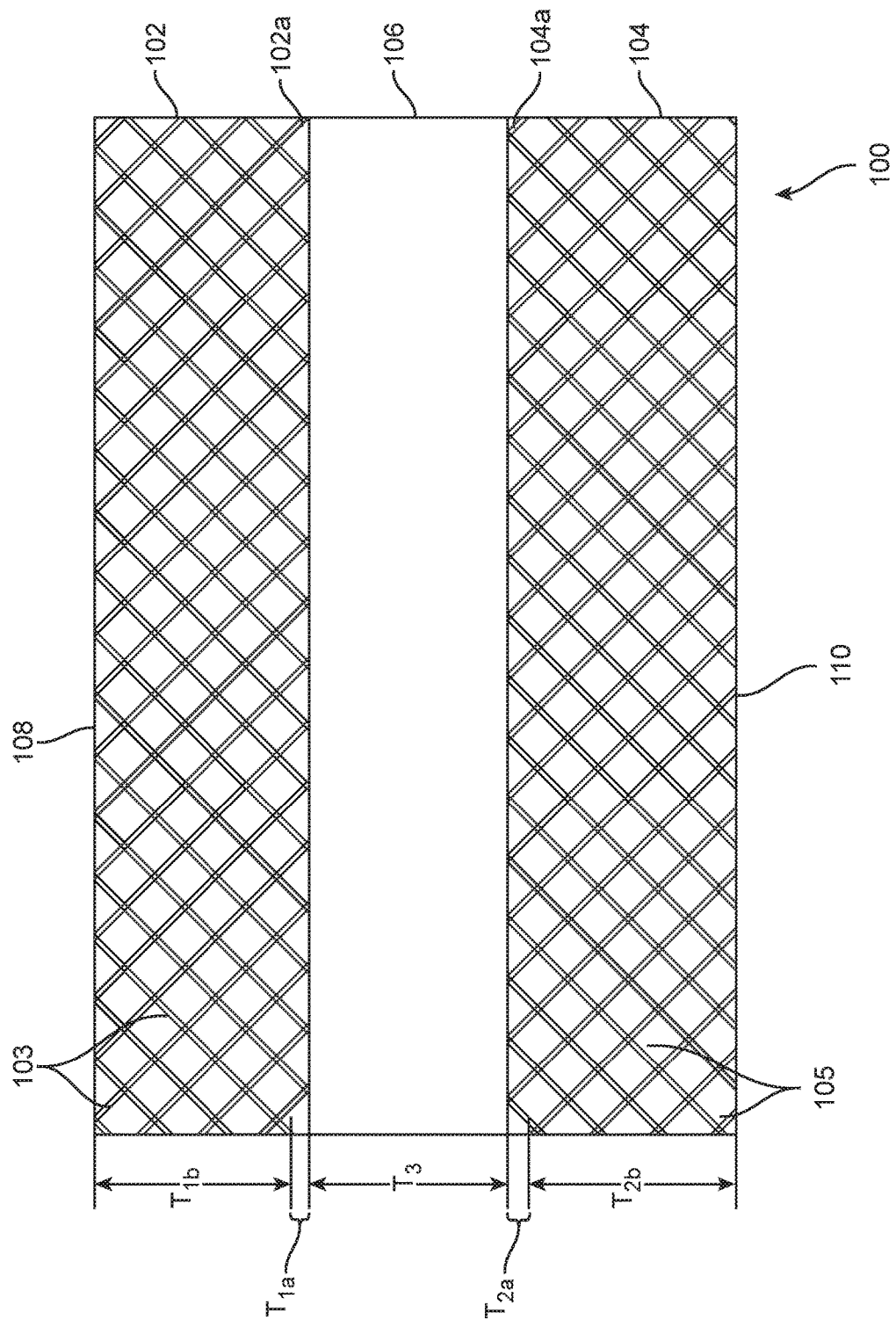
FIG. 3 is an enlarged schematic representation of the section of the implant of FIG. 2 showing an interface layer bonding two adjacent materials of the composite implant.

FIG. 3 is an enlarged schematic representation of the section 100 of the implant of FIG. 2 showing interface layers bonding two adjacent materials of the composite implant. FIG. 3 shows the top layer 102 with a top surface 108 for contacting the skull, a bottom layer 104 with a bottom surface 110 for contacting dura mater, and a middle layer 106. Top layer 102 includes an interface layer or region 102a and bottom layer 104 includes an interface layer or region 104a that include polymeric material of middle layer 106 dispersed around fibers 103 and 105, respectively. There is no polymeric material in top and bottom layers 102 and 104 outside of the interface layer or region. The thickness $T_1$ of top layer 102 includes a thicknes $T_{1a}$ of interface layer 102a and a thickness $T_{1b}$ of the region outside of the interface layer. The thickness $T_2$ of bottom layer 104 includes a thicknes $T_{2a}$ of interface layer 104a and a thickness $T_{2b}$ of the region outside of the interface layer.

The second porous polymeric layer may be impregnated through exposure of the second porous polymeric layer to a collagen solution or dispersion. The exposure to the collagen solution or dispersion may be performed by dip coating the second porous polymeric layer in the collagen solution or dispersion followed by drying in a vacuum oven. The dip coating may include completely immersing the composite polymer structure when it is desired to have a top layer that includes both collagen and mineral material. Alternatively, only the second porous polymeric layer may be immersed in the collagen solution or dispersion to impregnate only the second porous polymeric layer with collagen. The collagen content of the collagen solution may be 0.01 to 5 wt %, or more narrowly, 0.05 to 2 wt %, 0.1 to 1 wt %, or 2 to 10%.

The first porous polymeric layer may be impregnated through exposure of the first porous polymeric layer to a solution or solutions including calcium and phosphate ionic groups. The exposure of the first porous polymeric layer may be by soaking for by floating the first porous polymeric layer in a saline solution including calcium and phosphate salts. Alternatively the exposure may be performed by sequentially soaking or floating the first porous polymeric layer in a saline solution including calcium and then a solution of phosphate. The composite structure may be baked during or after the exposure at a temperature of 25 to 110° C. The calcium salts may include calcium chloride, calcium fluoride, calcium nitride, or any combination thereof. The phosphate salts may be ammonium phosphate or phosphoric acid.

A concentration of the calcium salts may be 0.001 to 1 mol/L, or more narrowly, 0.001 to 0.05 mol/L or 0.002 to 0.01 mol/L. A concentration of the phosphate salts may be 0.001 to 1 mol/L, or more narrowly, 0.001 to 0.05 mol/L or 0.001 to 0.01 mol/L.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The term "about" when modifying a numerical value may include the numerical value and plus or minus 1%; plus or minus 5%; plus or minus 10%; or plus or minus 20% of the numerical value. For example, "about 10 mm" means (for plus or minus 10%) 10 mm, from 9 mm to 11 mm, 9 mm to 10 mm, or 10 mm to 11 mm.

The recitation of numerical ranges by endpoints includes the endpoints and all numbers within that range.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

EXAMPLES OF IMPLANTS

Example 1

An example of a composite dura substitute implant is composed of three layers of PEKK material:
- The top layer is PEKK fabric is coated with bone-like apatite, has a porosity of 50%, and thickness of 2 mm.
- The middle layer of PEKK fabric has a porosity less than 0.1% and thickness of 0.5 mm.
- The bottom layer is PEKK fabric is coated with type I collagen, has a porosity of 50%, and thickness of 1 mm.

Example 2

An example of a composite dura substitute implant is composed of three layers of UHMWPE material:
- The top layer is Dyneema® fabric offered by DSM company, is coated with bone-like apatite, has a porosity of 60%, and thickness of 2 mm.
- The middle layer is a UHMWPE sheet with a porosity less than 0.1% and thickness of 0.5 mm.
- The bottom layer is Dyneema® fabric coated with type I collagen, has a porosity of 60%, and thickness of 1.5 mm.

Example 3

An example of a composite dura substitute implant is composed of three layers of PEEK material:
- The top layer is PEEK fabric coated with bone-like apatite, has a porosity of 50% and thickness of 1.5 mm.
- The middle layer is a PEEK sheet with a porosity less than 0.1% and thickness of 0.5 mm.
- The bottom layer is PEEK fabric coated with type I collagen, has a porosity of 50%, and thickness of 1 mm.

Example 4

An example of a composite dura substitute implant is composed of three layers of PMMA material:
- The top layer of PMMA fabric is coated with bone-like apatite, has a porosity of 30%, and thickness of 2.5 mm.
- The middle layer is a PMMA sheet with a porosity less than 0.1% and thickness of 0.1 mm.
- The bottom layer is a PMMA fabric coated with type I collagen, has a porosity of 30%, and thickness of 0.5 mm.

Example 5

An example of a composite dura substitute implant composed of three layers of PET material:
- The top layer is PET fabric coated with bone-like apatite with a porosity of 40% and thickness of 1.5 mm.
- The middle layer is a PET sheet with a porosity less than 0.1% and thickness of 0.5 mm.
- The bottom layer is PET fabric is coated with type I collagen, has a porosity of 40%, and thickness of 1 mm.

Examples of Preparing Dura Substitute Implants

Example 6

Preparing a PEEK Composite Dura Substitute Implant

Step 1: Electrospinning PEEK fibers to form PEEK fabric.
Step 2: Sandwich a dense, low porosity PEEK film between two pieces of PEEK fabric.
Step 3: Ultrasonically weld the above sandwiched PEEK construct so that the dense, low porosity PEEK film bonds with the PEEK films on both sides.
step 4: Dip the above bonded PEEK construct in an 80 wt % sulfuric acid solution for 1 min.
Step 5: Dip and soak one side of the PEEK construct in a solution containing 2.0 mM $Ca^{2+}$ and 1.0 mM $PO^{4-}$ for 5 d.
Step 6: Dip and soak another side of the PEEK construct in a solution containing at least 5% of Type I collagen for 1 d.
Step 7: Clean, dry, package and sterilize (with Ethylene Oxide) the PEEK construct.

Example 7

Preparing a UHMWPE Composite Dura Substitute Implant

Step 1: Obtain commercially available UHMWPE fabrics woven from Dyneema® fibers.
Step 2: Sandwich a dense UHMWPE film between two pieces of UHMWPE fabric.
Step 3: Thermally treat the above sandwiched UHMWPE construct at a temperature of 90° C. so that the dense, low porosity UHMWPE film bonds with the UHMWPE films on both sides.
Step 4: Dip and soak the above UHMWPE construct in a 10M NaOH solution for 4 hr.
Step 5: Oxygen plasma treat the above UHMWPE construct for 30 min.
Step 6: Dip and soak one side of the UHMWPE construct is a solution containing 2.0 mM $Ca^{2+}$, and 1.0 mM $PO^{4-}$ for 5d.
Step 7: Dip and soak another side of the UHMWPE construct in a solution containing at least 5% of Type I collagen for 1 d.
Step 8: Clean, dry, package and sterilize (with EO) the above UHMWPE construct.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

The invention claimed is:
1. An implantable dura substitute implant consisting of three layers:

a first porous layer consisting of a synthetic non-collagen polymer and an osteoconductive material;
a second porous layer consisting of the synthetic non-collagen polymer and a collagen component,
wherein the first porous layer does not include the collagen component,
wherein the second porous layer does not include the osteoconductive material; and
a middle layer consisting of the synthetic non-collagen polymer between the first porous layer and the second porous layer, wherein the middle layer is nonporous or has a lower porosity than the first porous layer and the second porous layer,
wherein the middle layer is a fabric layer made of woven or knitted fibers,
wherein the first porous layer is for contacting bone tissue and the second porous layer is for contacting dura mater upon implantation of the implant at the site of a dural defect in a patient,
wherein optionally the non-collagen polymer of the middle layer interpenetrates pores of the first porous layer at an interface between the middle layer and the first porous layer,
wherein optionally the non-collagen polymer of the middle layer interpenetrates pores of the second porous layer at an interface between the middle layer and the second porous layer,
wherein upon implantation the osteoconductive material facilitates growth of bone in the first porous layer from the bone tissue and the collagen facilitates dura repair and regeneration in the second porous layer, and
wherein the middle layer reduces or prevents leakage of cerebrospinal fluid (CSF) from the second porous layer and dura mater.

2. The implant of claim 1, wherein the synthetic non-collagen polymer is selected from the group consisting of poly aryl ether ketone (PAEK), polyethylene (PE), polyethylene terephthalates (PET), polymethylmethacrylate (PMMA), expandable polytetrafluorethylene (ePTFE), poly (lactic acid) (PLA), poly(glycolic acid) (PGA), and poly (lactic acid)-co-poly(glycolic acid) (PLGA).

3. The implant of claim 2, wherein the PAEK is selected from the group consisting of poly ether ether ketone (PEEK) and poly ether ketone ketone (PEKK).

4. The implant of claim 2, wherein the PE is ultra-high molecular weight polyethylene (UHMWPE).

5. The implant of claim 1, wherein the collagen component is derived from bovine tissue or porcine tissue.

6. The implant of claim 1, wherein the first porous layer is composed of fibers consisting of the non-collagen polymer and a coating on the fibers consisting of the osteoconductive material.

7. The implant of claim 6, wherein the non-collagen polymer is PEKK.

8. The implant of claim 6, wherein the non-collagen polymer is UHMWPE.

9. The implant of claim 1, wherein the second porous layer is composed of fibers consisting of the non-collagen polymer and a coating on the fibers consisting of the collagen.

10. The implant of claim 1, wherein the first porous layer and the second porous layer have a porosity between 20 and 90%.

11. The implant of claim 10, wherein the porosity is between 30 and 80%.

12. The implant of claim 10, wherein the porosity is between 40 and 70%.

13. The implant of claim 1, wherein a pore size of the first porous layer and the second porous layer is between 10 and 1000 microns.

14. The implant of claim 13, wherein the pore size is between 20 to 800 microns.

15. The implant of claim 13, wherein the pore size is between 50 to 500 microns.

16. The implant of claim 1, wherein middle layer is nonporous.

17. The implant of claim 1, wherein the middle layer has a porosity between 0 and 10%.

18. The implant of claim 1, wherein the osteoconductive material comprises a bone-like apatite material or a calcium phosphate material.

19. An implantable dura substitute implant consisting of three layers:
a first porous layer consisting of a synthetic non-collagen polymer and an osteoconductive material;
a second porous layer consisting of the synthetic non-collagen polymer and a collagen component; and
a middle layer consisting of the synthetic non-collagen polymer between the first porous layer and the second porous layer, wherein the middle layer is nonporous or has a lower porosity than the first porous layer and the second porous layer, wherein the middle layer is a fabric layer made of woven or knitted fibers,
wherein the first porous layer is for contacting bone tissue and the second porous layer is for contacting dura mater upon implantation of the implant at the site of a dural defect in a patient,
wherein upon implantation the osteoconductive material facilitates growth of bone in the first porous layer from the bone tissue and the collagen facilitates dura repair and regeneration in the second porous layer, and
wherein the middle layer reduces or prevents leakage of cerebrospinal fluid (CSF) from the second porous layer and dura mater.

20. The implant of claim 19, wherein the first porous layer is a fabric layer consisting of the polymer having a coating of the osteoconductive material.

21. The implant of claim 19, wherein the second porous layer is a fabric layer consisting of the polymer having a coating of the collagen component.

* * * * *